United States Patent [19]
Plicchi et al.

[11] Patent Number: 5,609,612
[45] Date of Patent: Mar. 11, 1997

[54] DEVICE FOR DETERMINING MYOCARDIAL FUNCTION AND CORRESPONDING PROCEDURE AND METHOD

[75] Inventors: Gianni Plicchi, Bologna; Giorgio Corbucci, S. Giovanni in Persiceto; Bruno Garberoglio, Turin, all of Italy

[73] Assignee: Sorin Biomedica Cardio S.p.A., Saluggia, Italy

[21] Appl. No.: 571,621

[22] Filed: Dec. 13, 1995

Related U.S. Application Data

[63] Continuation-in-part of Ser. No. 318,463, Oct. 5, 1994, Pat. No. 5,496,351.

[30] Foreign Application Priority Data

Oct. 5, 1993 [IT] Italy .................................. TO93A0729
Oct. 20, 1995 [IT] Italy .................................. TO95A0853

[51] Int. Cl.$^6$ ...................................................... A61N 1/365
[52] U.S. Cl. ................................................... 607/17; 607/6
[58] Field of Search ........................... 607/23, 17, 18, 607/3, 9, 6, 24

[56] References Cited

U.S. PATENT DOCUMENTS

| | | |
|---|---|---|
| 3,663,932 | 5/1972 | Mount et al. . |
| 3,716,059 | 2/1973 | Welborn et al. . |
| 3,805,795 | 4/1974 | Denniston et al. . |
| 3,853,462 | 12/1974 | Smith . |
| 3,986,828 | 10/1976 | Hoffman, Jr. et al. . |
| 4,047,252 | 9/1977 | Liebig et al. . |
| 4,193,137 | 3/1980 | Heck . |
| 4,209,859 | 7/1980 | Hoffman . |
| 4,301,809 | 11/1981 | Pinchak . |
| 4,360,031 | 11/1982 | White . |
| 4,600,017 | 7/1986 | Schroeppel . |
| 4,676,253 | 6/1987 | Newman et al. . |
| 4,763,646 | 8/1988 | Lekholm . |
| 4,917,115 | 4/1990 | Flammang et al. . |
| 4,922,930 | 5/1990 | Adkins et al. . |
| 4,936,304 | 6/1990 | Kresh et al. . |
| 4,989,611 | 2/1991 | Zanetti et al. . |
| 5,243,976 | 9/1993 | Ferek-Petric et al. . |
| 5,261,418 | 11/1993 | Ferek-Petric . |
| 5,271,392 | 12/1993 | Ferek-Petric . |
| 5,304,208 | 4/1994 | Inguaggiato et al. . |

FOREIGN PATENT DOCUMENTS

| | | |
|---|---|---|
| 0383732B1 | 8/1990 | European Pat. Off. . |
| 0495293A1 | 7/1992 | European Pat. Off. . |
| 0515319A2 | 11/1992 | European Pat. Off. . |
| 0541338A1 | 5/1993 | European Pat. Off. . |
| 2224752 | 10/1974 | France . |
| WO87/01947 | 4/1987 | WIPO . |
| WO91/13587 | 9/1991 | WIPO . |

OTHER PUBLICATIONS

Kresh et al., "An Interactive Microcompute–based Graphic System for Analysis of Cardio–Dynamic Function," AAMI 17th Annual Meeting, San Francisco, May 9–12, 1982, p. 65.

Kresh, "Pacing Sensors For Heart–Rate Control Biophysical Telemetry," Invited Speaker at 35th ACEMB Conference: Stimulation, Sensing, and Biocompatibility of Implanted Devices, Sep. 1982, pp. 1–4.

(List continued on next page.)

Primary Examiner—William E. Kamm
Assistant Examiner—Scott M. Getzow
Attorney, Agent, or Firm—Popovich & Wiles, P.A.

[57] ABSTRACT

The device senses Natural Heart Acceleration (NHA), isolating at least one segment (t) thereof corresponding to an isovolumetric phase, such as isovolumetric contraction (P1, P2) and/or isovolumetric relaxation (P3, P4). Preferentially, the action of isolation of the aforesaid segment is made starting from the electrocardiogram (ECG) signal. Among other things, the device may be used to carry out pacing functions (pacemaker, defibrillator, pacer cardioverter defibrillator) and/or to pick up, possibly by telemetry, data on the myocardial function and/or also to control a system of drug administration.

46 Claims, 6 Drawing Sheets

OTHER PUBLICATIONS

Kresh et al., "Effects of Left Ventricular Bypass on Intramyocardial Mechanics," Progress in Artifical Organs–1983, pp. 107–116.

Kresh et al., "The Intramyocardial Pressure: A Parameter of Heart Contractility," Heart Transplantation/vol. IV, No. 2, Feb. 1985, pp. 241–264.

Kresh et al., "Continuous Intraoperative Monitoring of Myocardial Tissue Pressure: Experimental and Clinical Results," American College of Surgeons 1985 Surgical Forum, vol. XXXVI, pp. 301–303.

Konigsberg et al., "Implantable Accelerometer for Telemetry," 3rd International Symposium on Biotelemetry, Pacific Grove, CA, May 17–20, 1976. (Computer abstract only).

"Ultrasonic Measurements In Vivo," Journal of Applied Physiology, vol. 74, No. 3 Mar., 1993, (advertisement).

Schipperheijn et al., "Contractility Studies Using a Cathetertip Accelerometer in the Left Ventricle," International Conference on Biomedical Transducers, Nov. 7, 1975, Paris, Exploration Cardio–Vasculaire, pp. 55–56.

Cai et al., "A Versatile Ultrasonic Ranging System," Sensor Review, vol. 13, No. 1, 1993, pp. 22–25.

"Winziger Beschleunigungsmesser–Chip Für Herzimplantation," Nachrichten Elektronik, vol. 33, No. 2, Feb. 1979, p. 63. (Translation included).

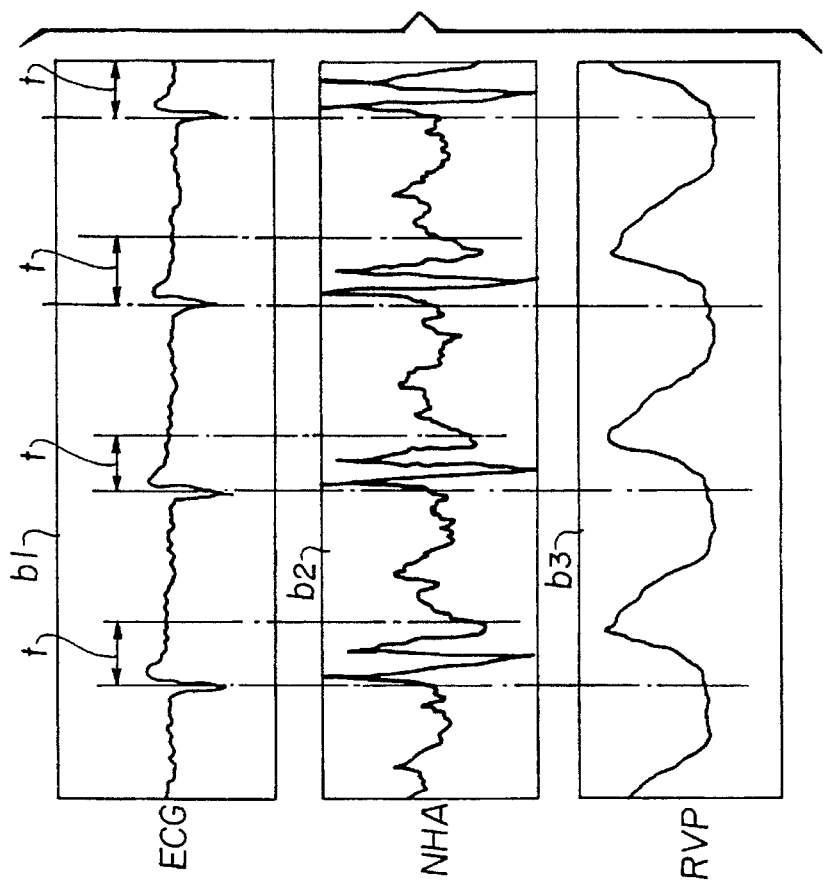
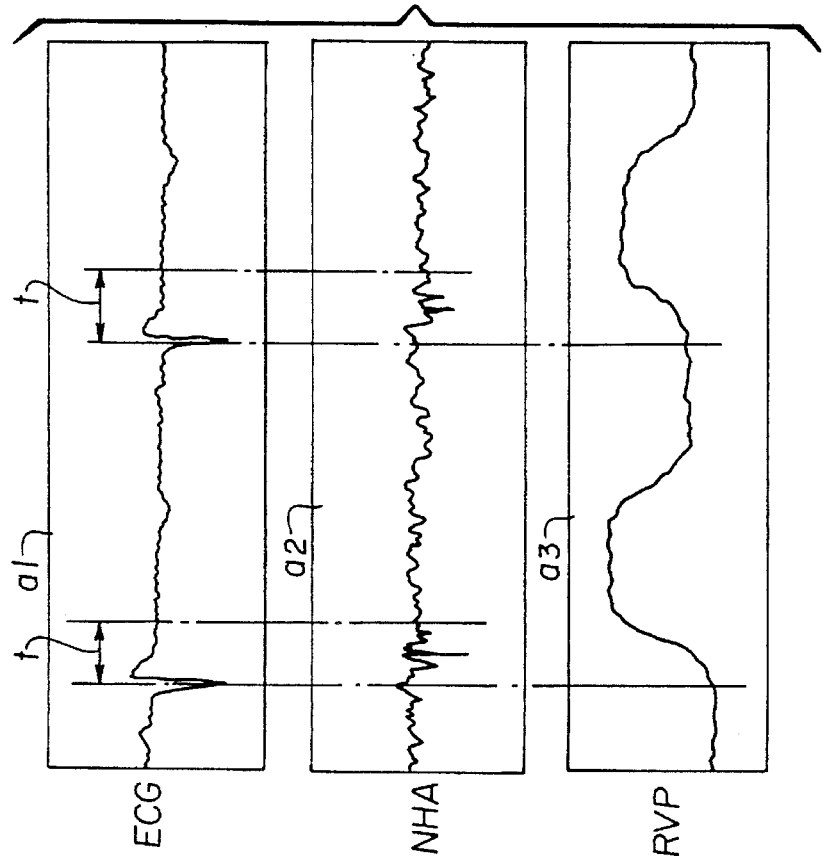

DEVICE FOR DETERMINING MYOCARDIAL FUNCTION AND CORRESPONDING PROCEDURE AND METHOD

This is a continuation-in-part of U.S. patent application Ser. No. 08/318,463 filed Oct. 5, 1994 now U.S. Pat. No. 5,496,351.

FIELD OF INVENTION

The present invention refers in general to the determination of the myocardial function by the use of accelerometric devices. More particularly, the invention relates to a device for determining myocardial functions and providing treatment responsive thereto.

BACKGROUND OF THE INVENTION

U.S. Pat. No. 5,304,208, incorporated herein by reference, describes a pacemaker of the rate-responsive type which includes an accelerometric sensor located in the pacing lead with the aim of making the pacing rate of the device depend on a parameter obtained by processing the signal of the Natural Heart Acceleration (NHA). U.S. Pat. No. 5,304,208 discloses the analysis of the entire signal which describes the NHA, and in particular the identification of the peak value, the calculation of the mean, and the possible identification of the atrial and ventricular phases; contemplating the utilization of the NHA signal for both single-chamber and dual-chamber cardiac pacemakers, for antiarrhythmic pacing devices and for implantable defibrillators, i.e., the so-called Pacer Cardioverter Defibrillators (PCDs). U.S. Pat. No. 5,304,208 differentiates the principles of measuring acceleration from those of measuring the blood pressure inside the ventricle and its derivative with respect to time. The same considerations can be extended to U.S. Pat. No. 4,936,304, where a cardiac pacemaker of the rate-responsive type is assumed, in which the pacing rate is regulated by the processing of intramyocardial stresses measured by inserting inside the myocardium a pressure meter of the type conceptually similar to the one used for measuring the ventricular blood pressure. Consequently, well documented from U.S. Pat. No. 5,304,208 is the substantial difference existing between the measurement of acceleration, where the accelerometric sensor is contained in an undeformable capsule, and the pressure transducers that are equipped with a deformable membrane which enables the pressure to be transduced into a measurable force.

The limitations in the use of the NHA signal according to the procedure described in U.S. Pat. No. 5,304,208 are based on the fact that, since the cardiac mass is subject to overall movements deriving from inertial reactions which are difficult to foresee and are due to the simultaneous phases of aortic and pulmonary ejection, and in association with these the movements themselves of the specific segment of endocardium in which the lead is inserted with the accelerometer, it may prove difficult from the mere reading of the accelerometric signal of NHA as a whole, to deduce which part is due to the overall movement and which expresses the muscular dynamics of the myocardium underlying the surface of the endocardium on which the accelerometer is set.

SUMMARY OF THE INVENTION

The present invention, therefore, sets itself the purpose of further improving upon U.S. Pat. No. 5,304,208, above all as far as the precision and reliability of the sensing action is concerned. According to the present invention, this purpose is achieved in a device having the characteristics referred to specifically in the claims that follow. The invention refers also to the corresponding method for determining the myocardial function.

In the form of implementation preferred at the moment, the invention includes an implantable micro-accelerometer and corresponding electronic circuits located on a lead, e.g., as described in U.S. Pat. No. 5,304,208. Further, the continuous measurement of the electrocardiogram is made with electrodes, one of which coincides with the container of the accelerometer, providing identification of one or more segments (either phases or intervals) of the signal that indicates the NHA of particular importance for determining the cardiac function. For instance, one can isolate an interval of time which comprises a phase of the cardiac cycle, e.g., the isovolumetric pre-ejection phase. Since total movements of the cardiac mass as a reaction to the expulsion phases do not occur, the signals that may be detected by the accelerometer derive solely from the contraction of the myocardial wall which precedes ejection.

Likewise, it is possible to isolate another time interval which contains the isovolumetric relaxation phase. Since there do not occur total movements of the cardiac mass as a whole, the accelerometric signals are indicative of the elastic behavior of the ventricular wall. Furthermore, from the analysis of the ventricular ECG, it is possible to recognize (using techniques which themselves are already known) the presence of arrhythmias which, since they alter the physiological rhythms and the physiology of cardiac mechanics, may lie at the root of errors of determination of the myocardial function. The recognition of these arrhythmias makes it possible to isolate, in the context of the accelerometric signal, the anomalies induced by them, so enabling both their elimination and a separate analysis.

In particular, the present invention makes it possible to distinguish, in the NHA signal, the acceleration of the endocardial wall on which the electrode is fixed from the acceleration that the mass of the heart as a whole undergoes. The foregoing is of major importance for the purposes of measuring a quantity that represents the contractile function of the heart which, for its definition, must be evaluated in a way that is independent of the pressure load that the heart is required to overcome during the ejection phase, and hence exclusively during isovolumetric phases.

As provided above, an important characteristic of the invention consists in associating to the measure of endocardial acceleration one or more time intervals which comprise the phases during which each cavity of the heart is virtually immobile (by analysis of the endocardial ECG), for example the phase of isovolumetric contraction, in which the only mechanics that occurs consists in the tensioning of the ventricular walls in order to prepare the ventricles for the subsequent ejection phase. This phase is defined in physiology as the phase of isovolumetric contraction and is associated with displacements of the endocardium of the order of only one mm during the increase in intraventricular blood pressure.

Typically in the normal heart at rest, the phase of isovolumetric contraction starts a few milliseconds after the QRS of the endocardial ECG and lasts for not longer than approximately two hundred msec. In the paced heart this interval, measured starting from the pacing spike, may be even as much as approximately two hundred and fifty msec. The duration of the abovementioned phase is not constant and varies as a function of parameters, such as cardiac rhythm and physical activity. The apparent contrast between the formal identification of this phase as isovolumetric and the minimal movement of the endocardial wall is physiologically explained by the retroflexion of the tricuspid valve in the right atrium, which causes a modest variation in the volume of the ventricular cavity.

The physiological definition of contractility is referred to the elementary unit of the cardiac muscle and consists in the velocity of the contractile element ($V_{CE}$) in the absence of load. Therefore, measuring acceleration in this phase, in which the ventricular work is represented by the minimal variation in volume associated to the retroflexion of the flaps of the tricuspid valve and by the low pressure present physiologically in the right atrium into which the same tricuspid valve is retroflexed, can be used to represent, in an original and innovative way, the contractile function of the heart.

In similar fashion, the description of the motion of the endocardial wall expressed by NHA during the phase of isovolumetric relaxation is an effective way of representing the compliance of the myocardial wall, which is an important index of cardiac function. The advantage of measuring the characteristics of the motion detected with a direct physical measurement of the acceleration of a point of the endocardium is all the more evident when it is considered that the methods currently used in clinical practice for estimating the maximum intrinsic volume of the myocardium, $V_{MAX}$, are based on the extrapolation of the first derivative of the ventricular blood pressure dP/dt referred to the isovolumetric pressure. This model requires the assumption of a precise geometry of the cardiac mass and endodiastolic volumes to allow calculation of the intramyocardial stresses with the aim of making available parameters that might be compared between different patients. Unfortunately, the unavailability of a truly reliable geometric model and the documented lack of homogeneity of the stresses within the myocardial wall, which differentiates the behavior of the layers close to the endocardium from those close to the epicardium, nullifies all the extrapolations that have the ultimate aim of identifying the contractile element velocity, $V_{CE}$, universally acknowledged as expressing contractility.

The solution of the present invention enables direct measurement in loco of the acceleration, for example, in the isovolumetric contraction phase, and is superior to indirect methods of measurement. The range of application of the present invention is considerably greater than that of the rate-responsive pacemaker and extends to the vast sector of cardiovascular illnesses in which it proves advantageous, if not essential, to have available a continuous measurement of the myocardial function. The transcutaneous telemetric transmission of the accelerometric signal together with the endocardial ECG to an appropriate external recording monitor (built using miniaturized techniques) allows display of the current value of the contractile function and the memorization of the trend of these signals for long time intervals, guides the cardiologist in drug therapy and other medical treatment of the patient, and may even furnish audio-optical warnings that prompt the patient to take the prescribed drugs. Further, it is possible to automatically manage the continuous infusion of drugs through external pumps controlled by these telemetric signals. Finally, it is possible to integrate the device for measuring and processing acceleration and the endocardial ECG in the electronics of an implantable infusion pump that may be recharged externally according to technologies already present on the market, but which do not envisage control sensors.

The invention described above can be utilized in single- or dual-chamber pacemakers of the rate-responsive type where, unlike what is described in U.S. Pat. No. 5,304,208, the endocardial acceleration is used only in the phase of isovolumetric contraction. Finally, the present invention can be utilized in Pacer Cardioverter Defibrillators or PCDs, where the solution according to the invention proves extremely sensitive in the identification of tachycardias that are haemodynamically not efficient.

In brief, the solution according to the invention envisages associating with the NHA signal the recording of the endocardial ECG, with the aim of separating from the entire periodic beat-to-beat NHA signal (NHA(t)) one or more time intervals, for example the time interval which contains the isovolumetric contraction phase. This time interval can be chosen, for instance, as approximately two hundred msec following on the spontaneous QRS and approximately two hundred and fifty msec following on a possible cardiac pacing pulse delivered through the tip of the lead located in the apex of the right ventricle, which contains also the accelerometric sensor. The duration of this interval can of course be automatically adapted (e.g., reduced) according to the heart rate.

On the endocardial acceleration signal sensed in this phase of duration T it is possible to carry out, either singly or in association, any type of mathematical processing, such as, for example, the peak-to-peak value, which indicates the maximum variation of the signal in that interval, and/or the peak value, and/or the rectified mean value expressed by the relation:

$$\text{Rectified Mean Value} = \frac{1}{T} \int_{o}^{T} |NHA(t)| dt$$

$$\text{Root Mean Square Value } (RMS) = \frac{1}{T} \sqrt{\int_{o}^{T} NHA(t)^2 \, dt}$$

where this value is directly correlated to the energy content. Other processing operations are of course possible, including derivations and/or integrations, also cascaded ones, to obtain signals of velocity and displacement.

In the form of implementation at present preferred, a device for the bi-directional transcutaneous telemetric transmission of data is associated with the device for sensing and processing acceleration and ECG, with the dual purpose of transmitting to an external receiver device both the endocardial ECG and the acceleration as sensed and/or as data processed in the phases identified starting from the ECG, as previously described. In the opposite direction the external device makes it possible to program the calibrations and to drive the implanted device in a complete way.

To this implanted system for measuring, processing, and transmitting data, which can mean for the cardiologist a product that can be of support in conventional therapeutic choices, it is possible to associate different therapeutic devices, either implantable or otherwise, where in the case of implantable ones the circuitry, mechanics and batteries can be contained in the same device that comprises the means of measuring, processing and transmitting bi-directional data.

In particular, this category of integrated devices includes a single- or dual-chamber cardiac pacemaker of the rate-responsive type driven by the processing of the heart acceleration signal in the isovolumetric contraction phase, associated or otherwise to other activity sensors. In this case, the ventricular lead performs the triple function of containing the accelerometer, the pacing electrodes, and the endocardial ECG sensing electrodes, possibly coinciding with the pacing electrodes.

In identical manner in the sector of the electrical therapy of cardiac arrhythmias, the device for sensing, processing and telemetering of acceleration and ECG can be integrated in the structure of a PCD with the purpose of confirming the possible haemodynamic inefficiency of serious atrial and/or ventricular tachyarrhythmias requiring sequences of electrical pulses for therapeutic purposes and/or defibrillation shock.

Also, the usual presence of a lead implanted in the right ventricle renders integration in existing technologies of this sector simple; the high percentage of false positives (15–20%) in which a defibrillation shock is needlessly delivered renders highly important the possibility of associating a mechanical parameter, such as that derivable from heart acceleration, to the analysis of the ECG to confirm the inefficiency of the cardiac pump and hence the activation of the therapeutic electrical sequences.

In the sector of implantable pumps for the continuous administration of medications, the utilization of the invention makes it possible to achieve in a precise and reliable way a continuous dosage regulated by the need for cardioactive drugs. In this case, the lead in the right ventricle is implanted only with the aim of sensing acceleration and endocardial ECG even though it is possible to combine the latter together with the pathway used for intravenous infusion of the drug. The electronic circuitry of the device in this case is integrated in the circuitry of the pump which already conventionally envisages the utilization of a bi-directional telemetry device.

In the example of application considered at the moment to be of greater interest, the invention refers to an implantable sensor of the contractile function of the heart on which it is applied, or to the passive telemetric monitoring of this function, or to the determination of the pacing rate in an implantable pacemaker of the rate-responsive type, or to the determination of the moment in which to make the discharge or the therapeutic stimulation in a PCD, or to control actively the supply of cardio-active drugs through external or implantable infusion pumps, where the functions referred to above can be performed singly or in association as required in any combination and with any number thereof.

In this case, the sensor to which the invention refers consists of a micro-accelerometer located inside the tip of a lead of the type used in implantable pacemakers or defibrillators and which combines with the function of detecting acceleration that of sensing the endocardial ECG between the tip and a second electrode, which can consist of a ring set at a short distance from the tip, or the implanted metal container itself (containing the necessary circuitry or battery) in which the lead referred to above is inserted, in a way similar to the procedure followed in the system of cardiac pacemakers, in the apex of the right ventricle, so that in certain of the envisaged applications, such as the rate-responsive pacemaker and the PCD, it is possible to associate with the passive function of measuring acceleration and of sensing the endocardial ECG also the active function of pacing and defibrillation of the heart.

BRIEF DESCRIPTION OF THE DRAWINGS

FIGS. 3a and 3b consists of six time diagrams, a1, a2, a3, and b1, b2, b3, which illustrate the typical pattern of certain signals indicating cardiac activity.

FIG. 5a shows RV/dP/dt max, LVdP/dt max and peak endocardial acceleration (PEA) measured over 15 minutes during positive inotropic stimulation with a dobutamine infusion; FIG. 5b charts the same characteristics over a period of 60 seconds during occlusion of the pulmonary artery.

DETAILED DESCRIPTION OF THE PREFERRED EMBODIMENT

Figure 1:
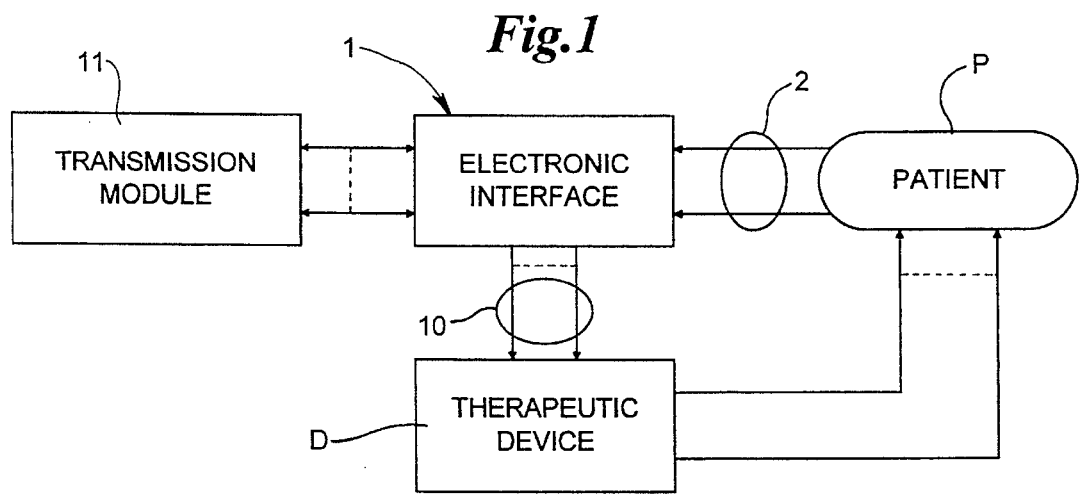
FIG. 1 illustrates schematically the general use of a device according to the invention.

The invention will now be described purely with the purpose of providing an example of application, without this application, however, in any way constituting a limit for the invention. In FIG. 1, block 1 represents an electronic interface device according to the invention having the purpose of sensing myocardial acceleration in at least one isovolumetric phase and of processing parameters derived therefrom. In a manner which will be described in more detail hereafter, electronic interface 1 receives, amplifies and filters the signal generated by the accelerometer and, triggered by endocardial ECG or pacing pulse, computes the peak endocardial acceleration during the isovolumetric phase according to a design known to those of skill in the art. This device is to be implanted in the body of a patient P.

Block 11 represents a conventional bi-directional transmission module for bi-directional data transmission between the inside and outside of the body of the patient for the purpose of monitoring myocardial acceleration and derived parameters of cardiac functionality, and for the purpose of programming operation of block 1. Such devices have been commonly employed for programming and for transcutaneously transmitting and receiving data from cardiac pacers and implantable defibrillators. Blocks 1 and 11 are preferably integrated in a single implantable device and are intended to operate together with a therapeutic device D, which may be a cardiac pacer, a PCD or a drug infusion pump. Device D is preferably implantable and, if possible, integrated with the device consisting of blocks 1 and 11. The device D is intended to carry out on the patient P a drug-administration intervention and/or an intervention of an electrical nature according to the processing of the myocardial acceleration and of the endocardial ECG performed by block 1 and block 11. It is, however, possible to create an implantable device consisting solely of blocks 1 and 11 with the exclusive aim of monitoring myocardial function. The device D can be replaced, for example, by a rate-responsive cardiac pacemaker or by an implantable cardiac defibrillator, or by a device for dosed administration of drugs. In any case, the characteristics and modes of operation of the device D are known to those of skill in the art. The characteristics of the device D, as well as the way in which it is connected to the body of the patient P, are not of themselves important for the purpose of understanding the invention.

In general, block 1 is connected to a lead, having a tip C inserted in the myocardium of patient P according to known criteria. The connection is made via input terminals 2 where, in 2a, there is present an endocardial ECG signal, and in 2b, an endocardial acceleration, NHA(t), measured by a sensor, such as the one described in U.S. Pat. No. 5,304,208. These signals are referred to a second reference electrode consisting of a ring located on the lead or of the metal container of the therapeutic device D, normally implanted subcutaneously.

Typical patterns of the signals are shown in diagrams a1 and b1 (ECG), and a2 and b2 (NHA(t)) of FIG. 3. Diagrams a3 and b3 represent the right ventricular pressure signal (RVP) sensed with a known transducer external with respect to the system described. The time scales of the superimposed diagrams coincide with one another. These signals were obtained in the course of experimental tests on animals (sheep) and refer to a situation of rest (Diagrams a1, a2 and a3) and to a pharmacological pacing phase carried out with intravenous injection of dobutamine (Diagrams b1, b2 and b3).

Figure 4:
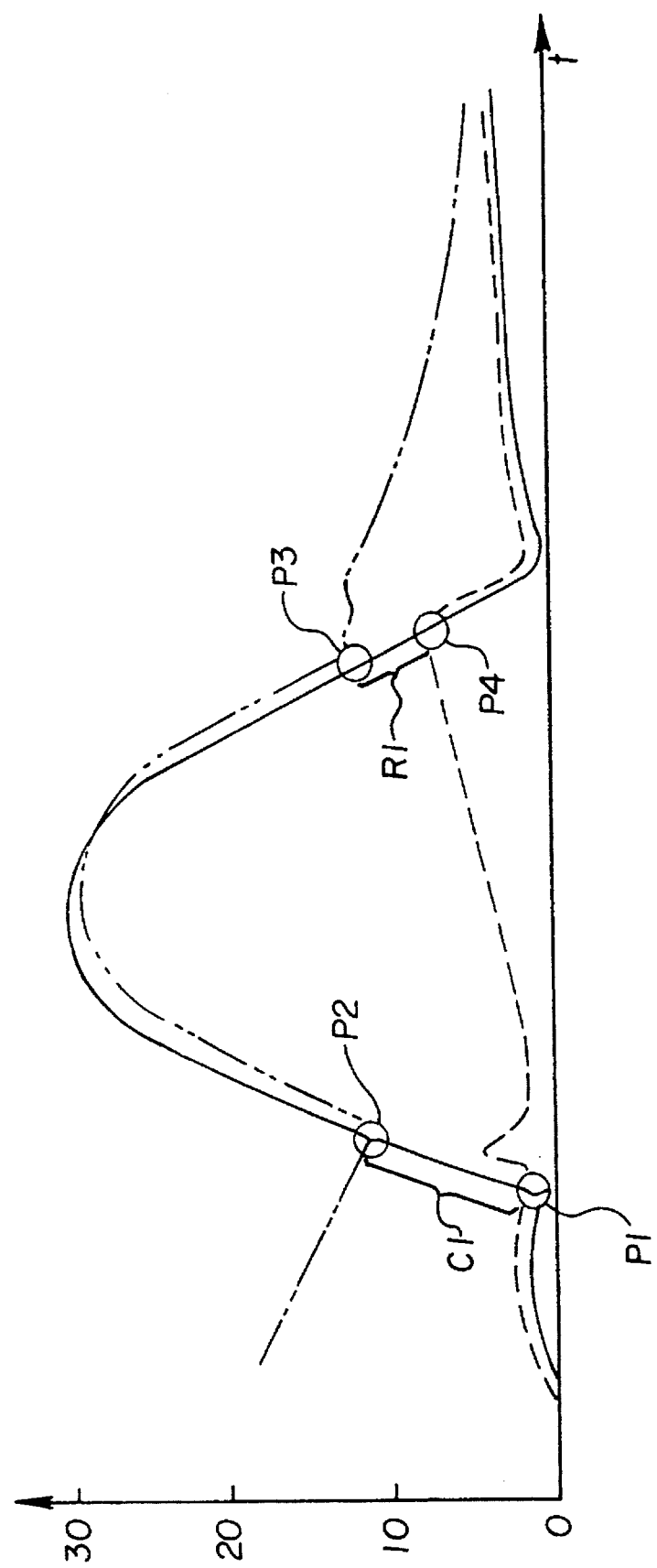
FIG. 4 is an ideal representation of the blood pressure wave recorded in the right side of the heart.

The diagram of FIG. 4 illustrates schematically the pattern over time of blood pressure (mm Hg on the ordinate) in the right hand side of the heart during one complete heart cycle. In particular, the solid line indicates the right ventricular pressure (RVP), while the dashed line and the dashed-and-dotted line indicate the pressure in the atrium and in the pulmonary artery, respectively. Points P1 and P2 identify the phase of isovolumetric contraction (CI), while points P3 and P4 identify the phase of isovolumetric relaxation (RI).

Figure 2:
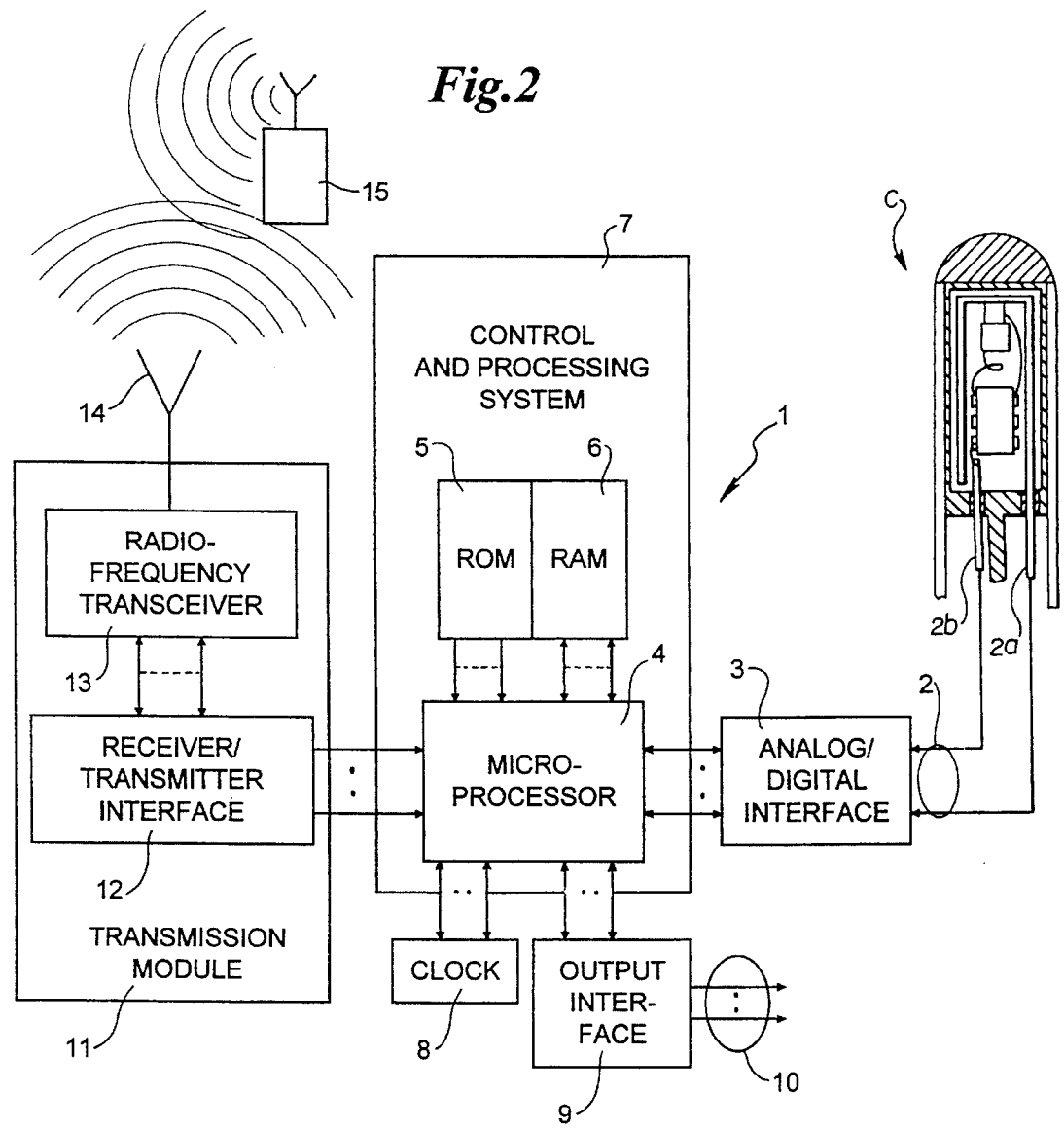
FIG. 2 illustrates, in the form of a circuit block diagram, the internal structure of the device according to the invention.

In FIG. 2, the signals 2a and 2b are operably coupled to analog-digital interface 3. The interface 3 transfers the signals supplied by the electrode 2a and the accelerometer 2b, converted into digital form, to the input of microprocessor 4. The latter constitutes, together with the respective memories, for instance of a ROM 5 and RAM 6, a control and processing system 7. Processing system 7 is the computing system of the device and operates to process the signals received (2a and 2b) according to the algorithm and programmed data stored in the memories. Its design is known to those of skill in the art. Associated with microprocessor 4 is clock 8 and output interface module 9 intended for driving, by means of corresponding output terminals 10, therapeutic device D. Bi-directional telemetric device 11 comprises receiver/transmitter interface 12 connected to the micro-processor 4, as well as radio-frequency transceiver 13, connected in bi-directional transmission to interface 12 and to transceiver antenna 14.

The process and control circuit 7 superintends all the operating phases of the device and processes the data coming from the adjacent interfaces. For this purpose, the ROM memory 5 serves preferentially as a program memory, while the RAM memory 6 serves preferentially as a memory for processing and maintaining the data programmed and saved by the microprocessor 4 itself, according to the processing carried out.

Transceiver 11 carries out the exchange of information between external programmer device 15 and control system 7. In particular, it performs the functions of receiving programmed parameters form outside and of transmitting the stored values to the RAM memory 6. Typically, the data transmitted regard the parameters processed by the system, measurements made or checks on the correctness of interaction between the external programmer and the implanted device itself. The transmission and receipt of data between the implantable device and the external programmer 15 takes place at radio frequencies. The processes referred to are achieved according to technical characteristics which are themselves well-known to those working in this sector.

Clock 8, which is also programmable, is able to supply the programming system with the time reference essential for a correct time base that refers to all the measurements.

Analog/digital interface 3 is typically equipped with a circuit for ventricular sensing which is able to recognize the electrical activity of the right ventricle and to discriminate it from interference coming from other sources, as well as with a circuit for amplification and analog-digital conversion of the signal of heart acceleration coming from the accelerometer located in the tip of the lead. This interface, therefore, sets in communication the endocardial sensing lead and the acceleration sensor with the device for processing and controlling information 7. In particular, the device connected to the terminal 2a is built using the same technology utilized by current cardiac pacemakers and by PCDs for performing the same function, while the device connected to the terminal 2b is built as illustrated in U.S. Pat. No. 5,304,208.

The processing operations performed by the system 7 on the signals coming from the terminals 2a and 2b have, in the first place, the purpose of analyzing the ECG signal (terminal 2a) in order to identify phases and/or events that are significant from the electrological point of view, for example, QRS and/or the T wave, measuring both amplitude and duration. Also sensed are parameters such as the frequency and period of the beat. All this is achieved on the basis of criteria which in themselves are known.

Starting from the analysis of the ECG signal, the system 7 processes the NHA(t) signal, isolating, within the signal, certain given time phases (segments) that constitute phases having an important haemodynamic meaning, for instance, isovolumetric contraction or isovolumetric relaxation, these being phases in which the dynamics of the heart wall is not perturbed by overall movements of the entire cardiac mass as a reaction to the ejection phases. For example, the control and processing system 7 is able to identify, in the context of the acceleration NHA(t), a segment t (see FIG. 3) immediately subsequent to the spontaneous QRS, within which the isovolumetric contraction phase occurs. In the presence of the cardiac pacing function, the system 7 identifies a segment (t+Δt, where Δt is of the order of approximately fifty msec) from the possible ventricular pacing spike, which contains the isovolumetric contraction phase. In the case where the segment corresponding to isovolumetric relaxation is isolated, the system 7 refers to the T wave of the ECG, both in the event of a spontaneous beat and in the presence of pacing.

The time duration of the segment t that is isolated is not necessarily fixed. For instance, in the case where the segment within which the isovolumetric contraction phase occurs is isolated, it is possible to configure the system 7 to vary the duration t, in order to associate with an increase in the beat rate (whether spontaneous or stimulated) a reduction, which may be even quite considerable, in this duration, or conversely, to associate with a reduction in the former an increase in the latter.

An example of a therapeutic device utilizing the NHA signal segments, as isolated above, is a rate responsive pacemaker. The pacemaker may be either a single or dual chamber pacer. Such a pacemaker would include a pulse generator, an acceleration sensor, an ECG sensor and appropriate pacing electrodes for providing stimulation pulses to the atrium, the ventricle or both, depending on the patients' needs. The features of such a pacemaker have been generally discussed above in connection with FIGS. 1 and 2. The NHA signal is processed to calculate the peak-to-peak value. The peak-to-peak value as measured inside a time window containing an isolated phase of the cardiac cycle, such as the isovolumetric contraction phase, is identified as the Peak Endocardial Acceleration (PEA).

The PEA has been found in normal hearts to have excellent correlation with both dP/dt maximum of the right ventricle (RV) and dP/dt maximum of the left ventricle (LV). RV dP/dt maximum has been previously used in the field of cardiac pacing for driving the pacing rate in rate responsive pacemakers. However, the contractile function of the whole heart is largely dependent on the left ventricle where most of the muscular mass is found. There are some conditions of the heart where LV dP/dt maximum does not correlate with RV dP/dt maximum. Thus, during these conditions RV dP/dt maximum does not provide a reliable indication of the contractile function of the heart.

Figure 5A:
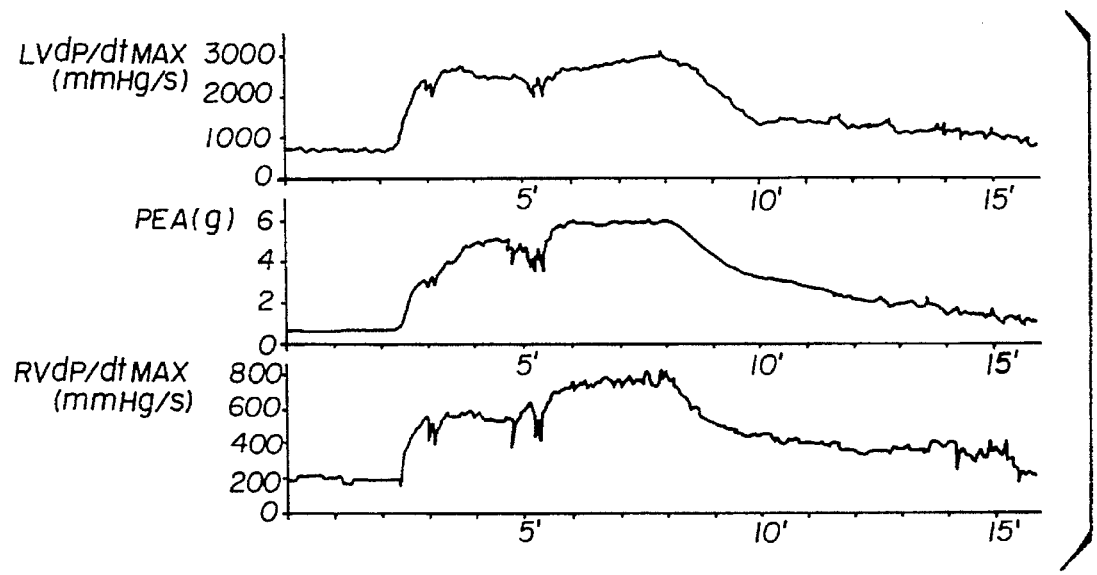
FIGS. 5a and 5b are graphs of data obtained from an experiment with an anesthetized sheep.
Figure 5B:
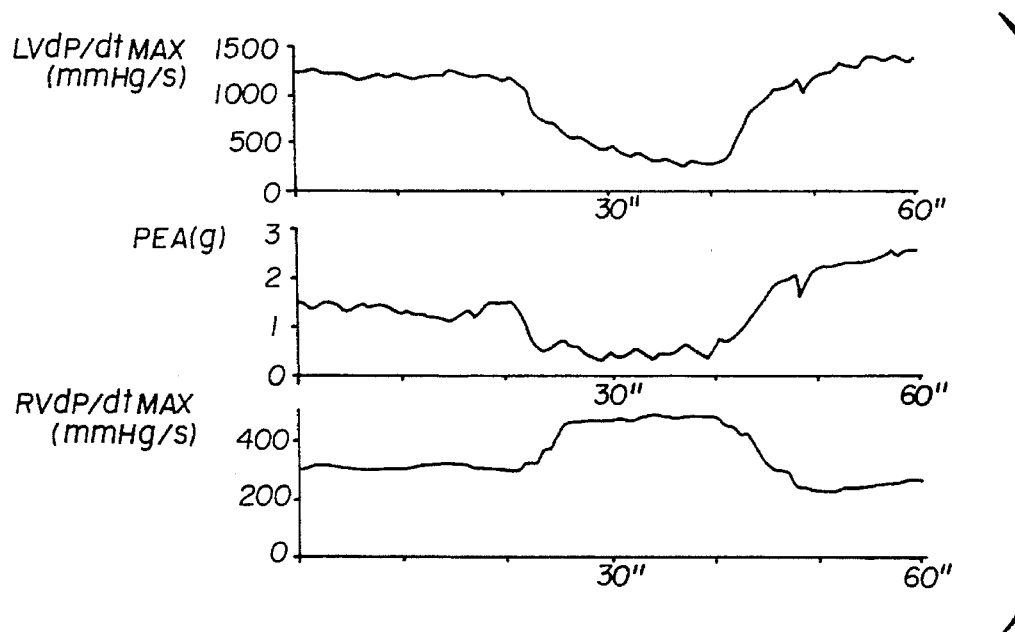

FIGS. 5a and 5b show data taken during experiments with an anesthetized sheep. FIG. 5a shows RV dP/dt maximum and LV dP/dt maximum measured over a period of 15 minutes during positive inotropic stimulation with a dobutamine infusion. PEA was measured with a sensor in the apex of the right ventricle over the same period of time. FIG. 5a shows a direct correlation between PEA, RV dP/dt maximum and LV dP/dt maximum over the 15 minute time period under normal heart conditions.

During the same experiment a condition of acute RV pressure overload and inadequate LV filling was created by occluding the pulmonary artery with a balloon. FIG. 5b shows RV dP/dt maximum and LV dP/dt maximum measured over a period of 60 seconds during the occlusion. PEA was again measured over the same 60 second period. The data in FIG. 5b shows a direct correlation between LV dP/dt maximum and PEA and demonstrates the dominance of LV contractility in modulating the PEA changes.

The data supports the conclusion that PEA measured from a sensor in the right ventricle provides an accurate indication of the contractile function of the whole heart, even under conditions where RV dP/dt maximum and LV dP/dt maximum do not correlate.

It has also been shown experimentally that PEA shows considerable correlation to heart rate under adrenergic stimulation such as during physical and mental stress tests. However, it has also been shown experimentally that PEA is not significantly dependent on heart rate variations induced by pacing at rest. This data supports the use of PEA as an effective physiological parameter upon which a rate responsive pacing system can be based.

Figure 6:
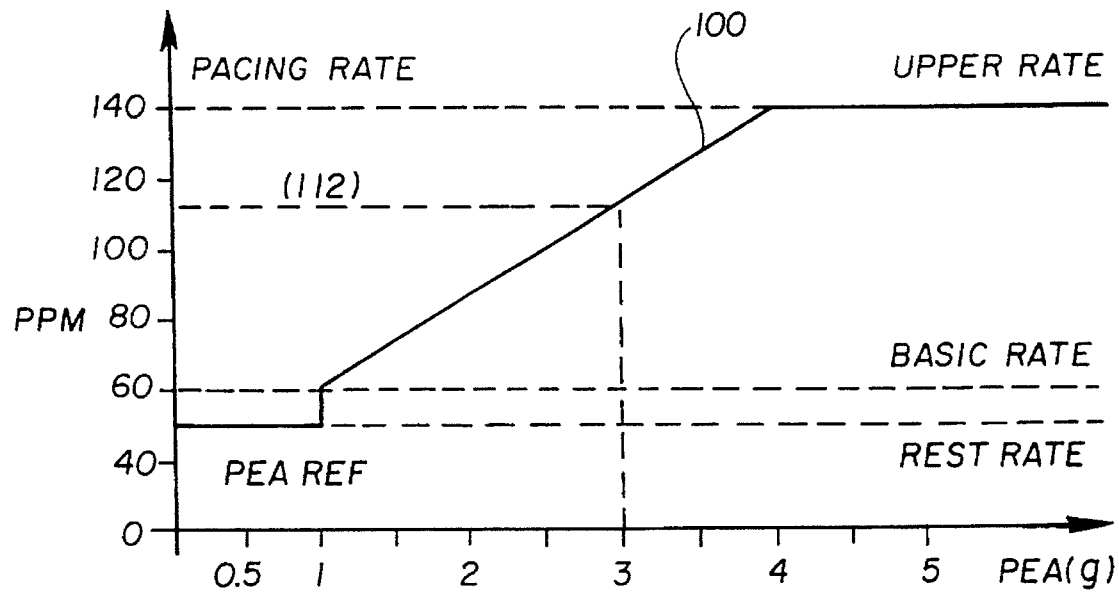
FIG. 6 is a graph of an algorithm used to adjust pacing rate of a rate responsive pacemaker.

FIG. 6 illustrates the graph of an algorithm based on the use of PEA to adjust the pacing rate of a rate responsive pacemaker similar to that discussed with respect to FIGS. 1 and 2. A PEA reference value (PEAREF) is selected to reflect the basal condition of the heart. PEAREF may be a programmable constant, or, preferably, is obtained by measuring PEA on a cycle-by-cycle basis and using a mobile averaging process with a long time constant. Thus, PEAREF is a floating value updated on a continuing basis based upon the average PEA value over a long period which may be from one hour or less to 48 hours or more. By selecting a sufficiently long time period over which to average PEA, the PEAREF value provides an accurate PEA basal value of the contractile function of the heart unaffected by short episodes of physical activity and/or mental stress. The system is self adjusting such that the value of PEAREF will change to accommodate long term changes in the basal state of the heart.

As seen in FIG. 6, the pacing rate adjusts from a lower limit or rest rate to an upper rate limit. In this case the rest rate is selected as 50 pulses per minute (ppm) and the upper rate is 140 ppm. These limits may be fully programmable so that they may be adjusted according to the needs or conditions of the patient. The basic rate is indicative of the value of the pacing rate under basal conditions, i.e. free of stress or physical activity. The rest rate may be programmed as an option to allow a lower heart rate at that point where the current value of PEA is just below PEAREF. In this example, the basic rate is set at 10 ppm over the rest rate. The rest rate is believed to be desirable to enable the heart rate to adjust to a lower value than the normal basal rate (basic rate) such as during periods of sleep. It should be noted however, that the difference between the basic rate and the rest rate can be programmed from zero to greater than 10 ppm.

The slope 100 between the basic rate and the upper rate serves as the rate response curve establishing the relationship between currently measured PEA and pacing rate. Although shown as being linear, slope 100 can be programmed to effect any desired nonlinear relationship between pacing rate and PEA.

The pacing rate is calculated cycle-by-cycle as a function of the difference between the currently measured PEA and PEAREF. For example, as illustrated in FIG. 6, if the current PEA is constant and equal to 3 g, the pacing rate will be approximately 112 ppm.

Figure 7:
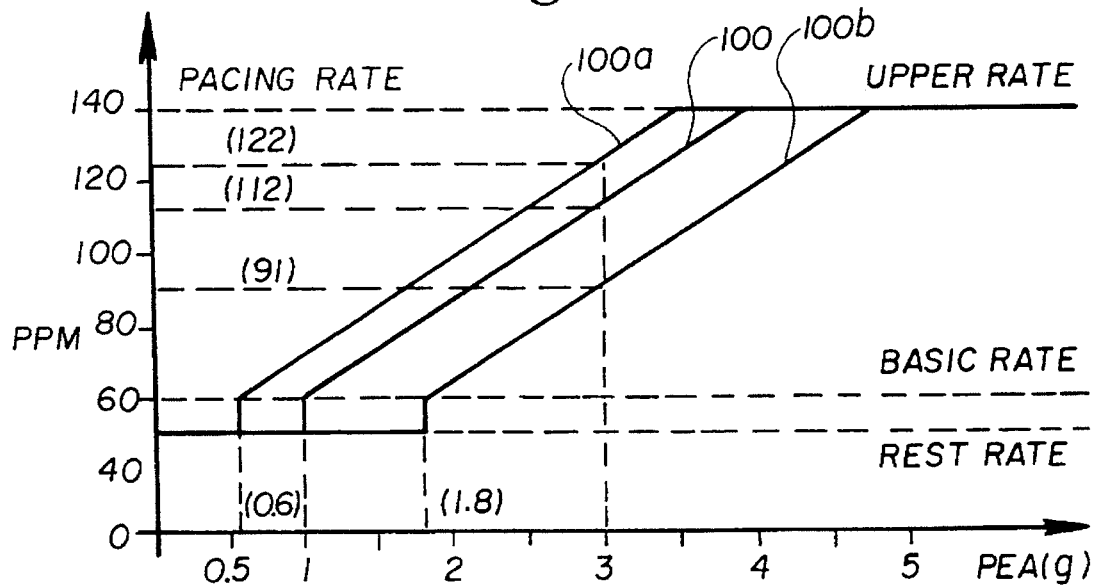
FIG. 7 is a graph illustrating the effect of a change in PEAREF on the pacing rate.

FIG. 7 illustrates the effect of a change in PEAREF on the pacing rate. If PEAREF decreases from 1 g to 0.6 g, slope 100 shifts to the left to the position of slope 100a. In that case a currently measured PEA of 3 g results in a pacing rate of approximately 122 ppm. If the PEAREF increases to approximately 1.8 g slope 100 shifts to the right to the position of slope 100b. At that position the pacing rate at a currently measured PEA of 3 g is approximately 91 ppm. It is important to note the differential nature of the algorithm upon which the pacing rate is based. Thus, for example, an increase in PEA of 1 g, i.e. from 2 g to 3 g, will cause the pacing rate to increase by the same amount whether the slope is in the position of slope 100a, 100 or 100b.

Figure 8A:
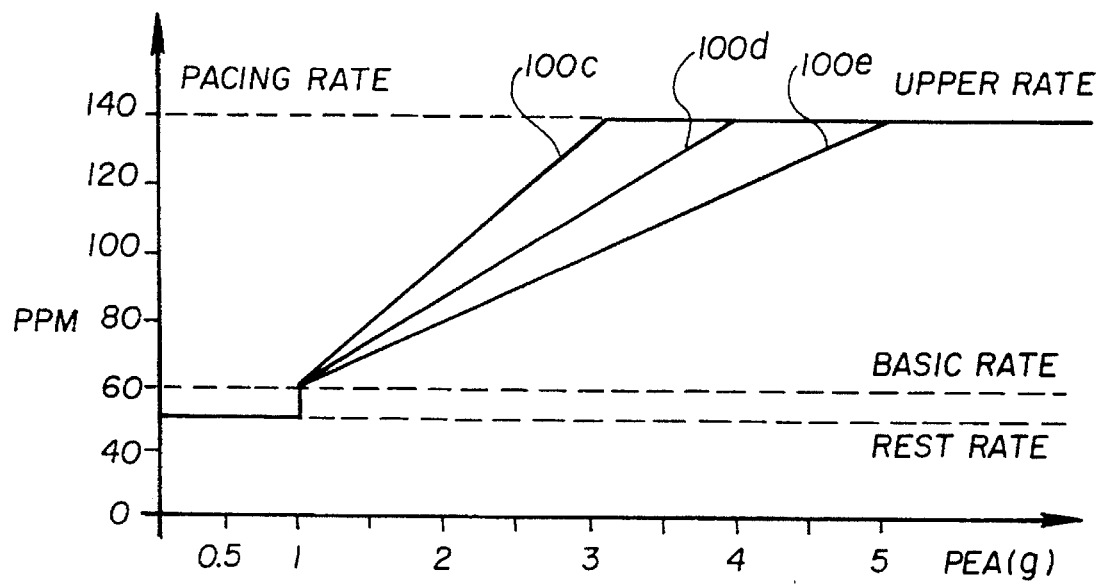
FIGS. 8a and 8b are graphs of rate responsive curves illustrating examples of the way of a pacemaker may be programmed to achieve a particular response desired for a patient.
Figure 8B:
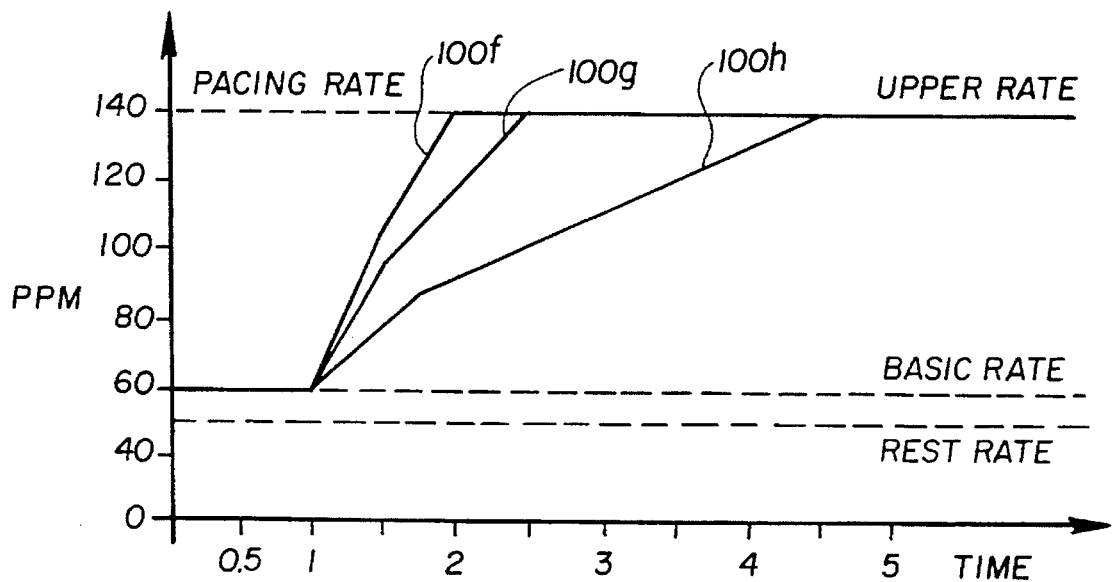

As seen in FIGS. 8a and 8b, the rate response curve may be programmed to have a higher or lower response depending on the needs of the patient. FIG. 8a illustrates a group of response curves 100c, 100d and 100e. Curve 100c has a higher pacing rate response than curve 100d, which in turn has a higher response than curve 100e. FIG. 8b illustrates a group of nonlinear rate response curves 100f, 100g and 100h having response rates varying from very fast (100f) to medium (100g) to slow (100h). FIGS. 8a and 8b show just a few examples of the way the pacemaker may be programmed to achieve the particular response desired for a patient.

In a further embodiment of the invention it is believed that PEA will serve as an effective parameter with which to control AV delay for those patients suffering from some form of heart conduction disease which may be associated with cardiomiopathy. It is known that cardiac output (CO), heart rate (HR) and stroke volume (SV) are related according to the following formula:

$$CO = HR \times SV$$

Since stroke volume is dependent in part upon AV delay it is clear that cardiac output will be optimized when the AV delay is set to allow optimal time for filling of the ventricles.

It is believed that there is a correlation between AV delay and PEA. Therefore, an algorithm based upon the relationship between AV delay and PEA may be used to set AV delay between upper and lower programmable limits. The algorithm would be used to optimize AV delay as a function of the currently measured PEA. This feature could be used alone or in combination with the rate responsive feature discussed above. Thus, the pacemaker would be able to adjust pacing rate and/or AV delay to provide a system which optimizes cardiac output according to a patient's needs.

Another important function of endocardial ECG analysis is the recognition of specific arrhythmic events, for example, ventricular extrasystoles which, since they alter the normal mechanics of heart contractions, could lead to an incorrect interpretation of the NHA signal. In this case, the identification of these events, based on the analysis of the ECG, makes it possible to exclude the mechanical effects of these anomalous events on the NHA signal from the subsequent processings. In the case of cardiac pacing, associating an effective NHA signal to the spike in the time interval set may enable the efficiency of the pacing to be ascertained.

The endocardial ECG signal may be processed not only for recognizing arrhythmias, but also for determining the pattern of heart rate, which is a very important parameter associated to NHA for evaluating the cardiac function. In particular, the system 7 proves able to evaluate the NHA/rate ratio, thus enabling identification of conditions of depression of the cardiac function in which to an increase in heart rate there corresponds an inadequate increase, or even a decrease in NHA. The availability of the ECG signal is moreover important for determining the so-called Heart Rate Variability (HRV) for measuring the sympathetic-vagal balance, as described in Patent No. EP-A-0 565 909.

On the NHA signal segments thus isolated, the system 7 can carry out the prescribed mathematical processing (calculation of peak-to-peak value, calculation of peak value, calculation of rectified mean value, or RMS, etc.).

In the control and processing system 7 are contained the decision-making mechanisms and the algorithms, obviously differentiated, which allow the application of a possible therapeutic phase whether of an electrical or of a pharmacological nature.

The output interface 9 transmits the command for intervention to the therapeutic device D, together with the values processed from the NHA and from the endocardial ECG, which are able to quantify the deviation from the optimal reference values, so allowing the device to intervene effectively.

In all due respect of the principle of the invention, the details and forms of implementation can be amply varied with regard to what has been described and illustrated above, without this entailing a departure from the sphere of the present invention.

We claim:

1. A pacemaker comprising:

a natural heart acceleration sensor;

a signal generator coupled to the sensor to provide a signal representative of the natural heart acceleration;

a processor connected to receive the signal for determining a value indicative of a characteristic of the signal during a selected time segment and calculating the difference between the determined value and a reference value, the processor being operative to select a pacing rate based upon the difference between the determined value and the reference value;

a pulse generator responsive to the selected pacing rate to generate stimulating pulses corresponding to the selected pacing rate; and at least one electrode for applying the stimulation pulses to at least one chamber of a patient's heart.

2. The pacemaker of claim 1 wherein the reference value is constant.

3. The pacemaker of claim 1 wherein the reference value is programmable.

4. The pacemaker of claim 1 wherein the reference value is a dynamic value calculated by the processor as the average of the determined value over a predetermined time interval.

5. The pacemaker of claim 4 wherein the predetermined time interval is in the range of between about one hour and about 48 hours.

6. The pacemaker of claim 4 wherein the selected time segment is a phase of a cardiac cycle.

7. The pacemaker of claim 6 wherein the phase of the cardiac cycle is an isovolumetric phase.

8. The pacemaker of claim 6 wherein the phase of the cardiac cycle is the isovolumetric contraction phase.

9. The pacemaker of claim 8 wherein the characteristic of the signal comprises peak endocardial acceleration.

10. The pacemaker of claim 9 wherein the processor is operative to select a pacing rate which includes an AV delay based upon the determined value.

11. The pacemaker of claim 4 further comprising an ECG sensor to generate a signal representative of the ECG and wherein the time segment of the natural heart acceleration signal which is selected corresponds to a predetermined portion of the ECG signal.

12. The pacemaker of claim 11 wherein the predetermined time interval is in the range between about one hour and about 48 hours.

13. The pacemaker of claim 12 wherein the predetermined portion of the ECG signal comprises an isovolumetric phase of the cardiac cycle.

14. The pacemaker of claim 12 wherein the predetermined portion of the ECG signal comprises the isovolumetric contraction phase of the cardiac cycle.

15. The pacemaker of claim 14 wherein the characteristic of the signal comprises peak endocardial acceleration.

16. The pacemaker of claim 15 wherein the processor is operative to select a pacing rate which includes an AV delay based upon the determined value.

17. A pacemaker comprising:

a natural heart acceleration sensor;

means for generating a signal representative of the natural heart acceleration;

means for selecting at least one time segment of the natural heart acceleration signal;

means for processing the signal during the selected time segment to determine a value indicative of a characteristic of the signal during the selected time segment;

means for determining the difference between the determined value and a reference value;

means for selecting a pacing rate based upon the difference between the determined value and the reference value; and means for providing stimulation pulses to at least one chamber of a patient's heart at the selected pacing rate.

18. The pacemaker of claim 17 wherein the reference rate is constant.

19. The pacemaker of claim 17 wherein the reference rate is programmable.

20. The pacemaker of claim 17 wherein the reference value is a dynamic value calculated by the processing means as the average of the determined value over a predetermined time interval.

21. The pacemaker of claim 20 wherein the predetermined time interval is in the range of between about one hour and about 48 hours.

22. The pacemaker of claim 20 wherein the selected time segment is a phase of the cardiac cycle.

23. The pacemaker of claim 22 wherein the phase of the cardiac cycle is an isovolumetric phase.

24. The pacemaker of claim 22 wherein the phase of the cardiac cycle is the isovolumetric contraction phase.

25. The pacemaker of claim 24 wherein the characteristic of the signal comprises peak endocardial acceleration.

26. The pacemaker of claim 25 wherein the processing means selects a pacing rate which includes an AV delay based upon the determined value.

27. The pacemaker of claim 20 further comprising an ECG sensor to generate a signal representative of the ECG and wherein the selection of the time segment of the signal which is selected corresponds to a predetermined portion of the ECG signal.

28. The pacemaker of claim 27 wherein the predetermined time interval is in the range of between about one hour and about 48 hours.

29. The pacemaker of claim 28 wherein the phase of the cardiac cycle is an isovolumetric phase.

30. The pacemaker of claim 28 wherein the phase of the cardiac cycle is the isovolumetric contraction phase.

31. The pacemaker of claim 30 wherein the characteristic of the signal comprises peak endocardial acceleration.

32. The pacemaker of claim 31 wherein the processor is operative to select a pacing rate which includes an AV delay based upon the determined value.

33. A method for controlling a heart pacemaker comprising:

sensing a natural heart acceleration of a patient;

generating a signal representative of the natural heart acceleration;

selecting at least one time segment of the natural heart acceleration signal;

processing the signal during the selected time segment to determine a value indicative of a characteristic of the signal during the selected time segment;

determining the difference between the determined value and a reference value;

selecting a pacing rate based upon the difference between the determined value and the reference value; and pacing at least one chamber of the patient's heart at the selected pacing rate.

34. The method of claim 33 further comprising calculating the average of the determined value over a predetermined time interval and using the result to continually update the reference value.

35. The method of claim 34 wherein the predetermined time interval over which the average of the determined value is calculated is in the range between about one hour and about 48 hours.

36. The method of claim 34 wherein the time segment selected is a phase of the cardiac cycle.

37. The method of claim 36 wherein the phase of the cardiac cycle selected comprises the isovolumetric phase.

38. The method of claim 36 wherein the phase of the cardiac cycle selected comprises the isovolumetric contraction phase.

39. The method of claim 38 wherein the characteristic of the signal which is determined during the processing step comprises peak endocardial acceleration.

40. The method of claim 39 wherein the signal is processed to select a pacing rate which includes an AV delay based upon the determined value.

41. The method of claim 34 further comprising sensing the ECG of the patient's heart and generating a signal representative of the ECG and wherein the time segment of the natural heart acceleration signal is selected to correspond with a predetermined portion of the ECG signal.

42. The method of claim 41 wherein the predetermined time interval over which the average of the determined value is calculated is in the range between about one hour and about 48 hours.

43. The method of claim 42 wherein the time segment selected is a phase of the cardiac cycle.

44. The method of claim 43 wherein the phase of the cardiac cycle selected comprises an isovolumetric phase.

45. The method of claim 43 wherein the phase of the cardiac cycle selected comprises the isovolumetric contraction phase.

46. The method of claim 45 wherein the characteristic of the signal which is determined during the processing step comprises peak endocardial acceleration.

* * * * *